(12) United States Patent
Poirier

(10) Patent No.: US 6,382,975 B1
(45) Date of Patent: *May 7, 2002

(54) MANUFACTURING A DENTAL IMPLANT DRILL GUIDE AND A DENTAL IMPLANT SUPERSTRUCTURE

(75) Inventor: Michel Poirier, Ste-Agathe-des-Monts (CA)

(73) Assignee: Technique d'Usinage Sinlab Inc., Blainville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/595,921

(22) Filed: Jun. 16, 2000

Related U.S. Application Data

(63) Continuation of application No. PCT/CA97/00984, filed on Dec. 18, 1997, which is a continuation of application No. 08/806,938, filed on Feb. 26, 1997, now Pat. No. 5,725,376.

(51) Int. Cl.⁷ .................................................. A61C 8/00
(52) U.S. Cl. ........................................ 433/173; 433/213
(58) Field of Search .............................. 433/172, 173, 433/213, 75, 215

(56) References Cited

U.S. PATENT DOCUMENTS

| | | |
|---|---|---|
| 3,078,580 A | 2/1963 | Galvez |
| 4,325,373 A | 4/1982 | Slivenko et al. |
| 4,767,328 A * | 8/1988 | Branemark .................. 433/173 |
| 4,906,191 A * | 3/1990 | Söderberg .................. 433/213 |
| 5,401,170 A | 3/1995 | Nonomura |
| 5,427,906 A * | 6/1995 | Hansen ........................ 433/173 |
| 5,527,182 A | 6/1996 | Willoughby |
| 5,630,717 A * | 5/1997 | Zuest et al. .................. 433/172 |
| 5,725,376 A * | 3/1998 | Poirier ........................ 433/172 |
| 5,857,853 A * | 1/1999 | Van Nifterick et al. ..... 433/213 |

FOREIGN PATENT DOCUMENTS

| | | |
|---|---|---|
| DE | 680 764 | 9/1939 |
| DE | 836 993 | 4/1952 |
| DE | 43 28 490 A1 | 3/1995 |
| DE | 195 10 294 A1 | 10/1996 |
| DE | 196 29 708 A1 | 2/1998 |
| EP | 0 215 765 | 3/1987 |

* cited by examiner

Primary Examiner—Ralph A. Lewis
(74) Attorney, Agent, or Firm—Swabey Ogilvy Renault; James Anglehart

(57) ABSTRACT

Dental implant drill holes and the shape of a dental implant superstructure are chosen by creating a computer model giving jawbone structural details, gum surface shape information and proposed teeth or dental prosthesis shape information. The computer model shows the bone structure, gum surface and teeth images properly referenced to one another so that implant drill hole position can be selected talking into consideration proper positioning within the bone as well as proper positioning with respect to the dental prosthesis. Similarly, manufacture of the dental implant superstructure used for fixed dental prosthesis or overdentures can be designed based on knowledge of the actual implant position referenced to an image of the gum surface and proposed dental prosthesis.

4 Claims, 9 Drawing Sheets

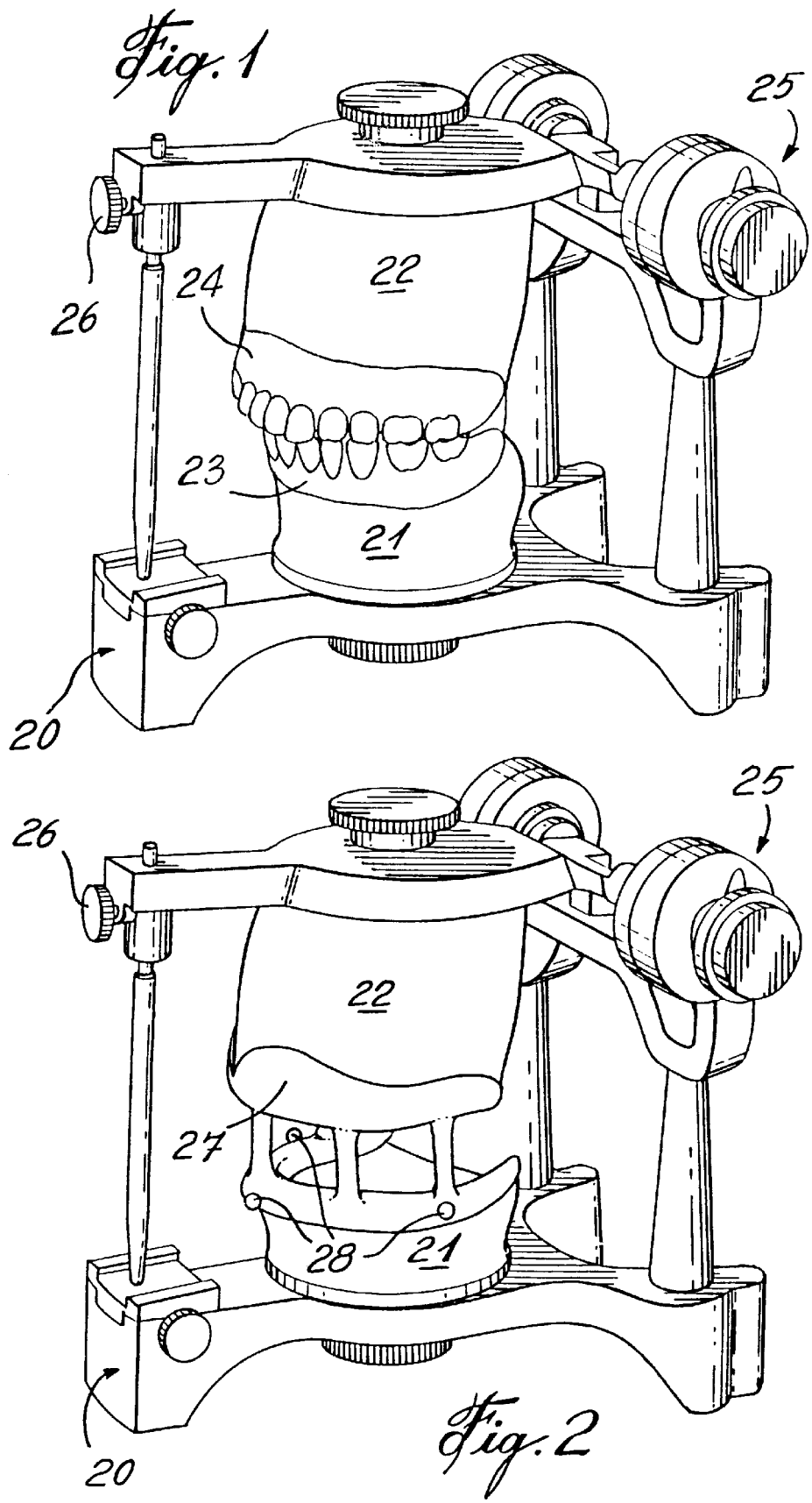

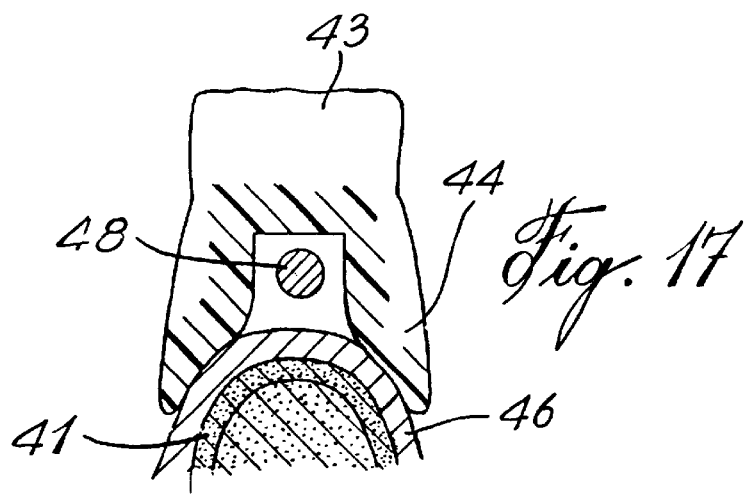
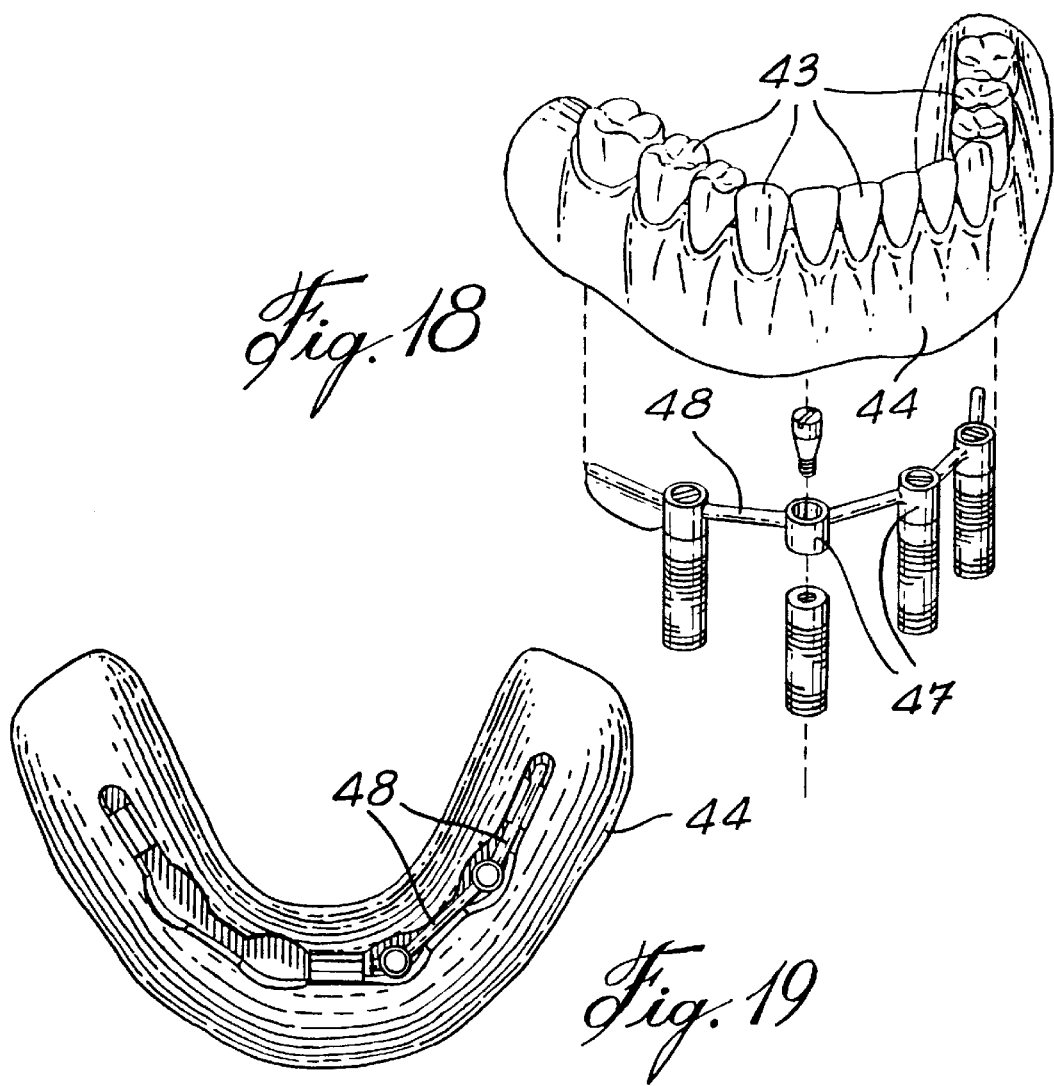

MANUFACTURING A DENTAL IMPLANT DRILL GUIDE AND A DENTAL IMPLANT SUPERSTRUCTURE

RELATED APPLICATION

This is a continuation of International PCT Application No. PCT/CA97/00984 filed Dec. 18, 1997 U.S. application Ser. No. 08/806,938, now U.S. Pat. No. 5,725,376 filed on Feb. 26, 1997 and issued on Mar. 10, 1998

FIELD OF THE INVENTION

The present invention relates to a method of manufacturing a dental implant drill guide. The invention also relates to a dental implant superstructure.

BACKGROUND OF THE INVENTION

It is known in the art to secure dental prostheses using dental implants secured in the upper or lower jawbone. It is also known in the art to mount a framework or superstructure to a number of implants, the superstructure being used to evenly support a set of false teeth or denture prostheses. Accurate placement within the jawbone of the implants is a difficult task. In International Patent Application No. PCT/IT94/00059, published Nov. 24, 1994 as WO 94/26200, there is described an adjustable guiding device for positioning dental implants in which it is possible for the dental surgeon to adjust a drill axis for each implant before proceeding to use the guiding device or drill template to guide the surgeon's drill for the purposes of preparing the drill hole for the implant. The guiding device disclosed in the International publication helps the dental surgeon to decide on the drill axis after viewing radiographic images of the radio-opaque tubular drill guide superposed the bone structure.

In the known prior art, the oral surgeon typically has difficulty deciding on a drill axis for the implants since the ideal position for the implants should be decided with knowledge of the jawbone structure into which the implant is to be inserted, knowledge of the position within the jawbone structure of the nerve tissue, the gum surface and the required position and dimensions of the false teeth or dentures to be supported by the dental implant. Of course, in the conventional manner of selecting the implant axis, the dentist or dental surgeon simply makes a best guess in light of his knowledge of the patient. Of course, this leads, in certain cases, to imperfections in the dental prosthesis. The imperfections may be lack of ideal support, unfavorable angulation of an implant causing a weakness in the implant which may cause failure over time, or a visually perceptible defect in the appearance of the prosthesis.

In the conventional method for the construction of the superstructure, a physical model of the patient's gums and dental implant heads is prepared on which the superstructure is built manually using molding and other techniques known in the art. The craftsman or technician skilled at manufacturing such dental superstructures takes into consideration the size and shape of the desired dentures to be placed over the superstructure when crafting the same. The procedure for manufacturing dental implant superstructures as is conventionally known in the art is time-consuming and sometimes results in imperfect structures or defects in the visual appearance of the dentures to be placed over the superstructure.

In U.S. Pat. No. 5,401,170 granted Mar. 28, 1995 to Nonomura, there is disclosed a method and apparatus for measuring by camera image the implant heads of the implants in the patient's mouth for the purposes of cutting a frame on which the prosthetic teeth will be arranged and baked. In the method disclosed, the construction of the frame or superstructure is carried out in the absence of a reference to the shape and position of the patient's ideal teeth position. Thus, as the dentures or artificial teeth are crafted on the frame or superstructure, care would be required during the manual process to ensure that the position of the teeth on the frame will match the opposed set of teeth in the patient's mouth.

OBJECTS OF THE INVENTION

It is a first object of the present invention to provide a method of manufacturing a dental implant drill guide or drill template which will result in a precise and accurate drill guide for selected drill holes. It is furthermore an object of the present invention to provide a method of manufacturing a dental implant superstructure in which information concerning the position of a plurality of dental implants mounted in a jawbone, the gum surface covering the jawbone and the fixed denture shape is all taken into consideration during the specification of the shape of the superstructure before the superstructure is precision made.

It is yet another object of the present invention to provide such methods which provide better accuracy and faster results than conventional methods.

It is yet another object of the present invention to provide a dental implant drill guide which is precise and easy to use such that drilling of the dental implant holes does not require expert skill and knowledge beyond the skill of basic dental surgery. It is furthermore an object of the present invention to provide tools which will reduce the number of visits a patient needs to make to the dental surgeon in order to have dental implants and a dental implant superstructure inserted.

SUMMARY OF THE INVENTION

According to a first aspect of the invention, there is provided a method of manufacturing a dental implant drill guide, comprising the steps of: (a) imaging a jawbone and tissue structure with a reference to a gum surface to produce a three-dimensional computer graphics model; (b) selecting at least one implant drill hole position for at least one dental implant using the said mode, the position being specified in three dimensions, including a hole termination point and orientation, and being referenced to the gum surface reference; (c) entering at least one set of implant drill hole position coordinates into a CNC device; (d) providing a drill template body having a first surface for mating with a gum surface of the jawbone; and (e) using the CNC device to provide a fixed orientation drill guide socket in the template body for each one of the at least one drill hole positions entered in step (c) with a corresponding position and orientation.

According to a second aspect of the present invention, there is provided a method of manufacturing a dental implant superstructure having a plurality of dental implant abutting flanges and a gum tissue overlying bridge to which a dental prosthesis can be attached, the method comprising the steps of: (a) obtaining an image of a gum surface; (b) obtaining an image of dentures or teeth to be placed over the gum surface; (c) obtaining dental implant position data defining a position and angular orientation of a plurality of dental implants mounted in a jawbone covered by the gum surface; (d) referencing the gum surface image, the teeth or denture image and the implant position data with respect to a common frame of reference; (e) generating a computer graphics model of the gum surface, the dentures or teeth and the dental implants; (f) selecting a shape of the overlying bridge using the model and specifying shape data; and (g) entering the shape data into a precision superstructure manufacturing device.

In the method of manufacturing a dental implant drill guide according to the present invention, the patient is typically edentured, namely, the patient has had all teeth pulled from the jawbone, and the jawbone has been given time to heal since the teeth were pulled. If the patient decides to proceed with dental implants and the placement of a superstructure for solidly securing dentures over the gum, a period of about 12 months is provided for from the time of pulling any remaining teeth from the jawbone before proceeding with the operation of inserting implants into the jawbone.

A medical image of the jawbone and tissue structure is obtained by using x-ray imaging, MRI or possibly nuclear imaging techniques to produce a three-dimensional computer graphics model which has a reference to the gum surface or some other fixed reference with respect to the patient's jawbone. Preferably, a radiographic scanner guide is used which is molded to conform to the shape of the patient's gums and which includes radio-opaque spheres whose positions with respect to the gum surface is known.

The primary advantage of the invention is that the oral surgeon may select the optimum position for dental implants using the three-dimensional computer graphics model of the jawbone and tissue structure. Selection of the drill hole positions using the computer graphics model is transferred to a CNC device for the purposes of providing fixed drill guide sockets in the template body for each one of the drill hole positions or position selected using the computer graphics model. While the model is three-dimensional, it may be convenient for the purposes of selecting the drill hole axis to use a two-dimensional representation of the jawbone and tissue structure, the two-dimensional view being displayed with a user controlled slice angle. Preferably, the dental surgeon will select the position for each implant drill hole, not only to position the implant in the optimum location within the jawbone, but also to result in a position of support which is suitable for supporting the dentures. Therefore, it is preferred to display, in addition to the three-dimensional computer graphics model of the jawbone and tissue structure, the patient's dentures in the proper spatial relationship with respect to the jawbone and tissue structure. This requires imaging the patient's dentures or teeth, and possibly gum structure, in addition to the jawbone and tissue structure, in such a way that all images are referenced with respect to one another to be integrated into the same three-dimensional computer graphics model.

While it would be possible to prepare the drill template body and provide it with the drill guide sockets using the CNC device, the drill template body is preferably molded on a physical model of the gum surface into which model the CNC device has previously drilled the desired implant drill holes. The drill holes in the physical model are used to build a mold for the drill guide sockets. This prevents the need to use the CNC device to produce fine details except for the precision drilling of the drill holes.

Imaging of the dentures or teeth to be placed over the gum surface and the imaging of the gum surface can be carried out by using laser camera imaging techniques known in the art. These images are preferably obtained using a physical model of the patient's gum surface, and the physical model is imaged in such a way that the images can be referenced accurately to the jawbone and tissue structure images.

In the method of manufacturing the dental implant superstructure according to the invention, the actual dental implant position data is obtained preferably by taking an imprint using transfers connected to the implants. Preferably, the imprint is taken using the same drill guide according to the invention with the sockets of the drill guide being large enough to receive the transfers and surrounding imprint material. Preferably, the positions and orientations of the transfers are physically measured along with a reference to the drill guide which will permit the relative positions of the implants to be known with a reference to a standard frame of reference. Using the standard frame of reference, it is possible to generate a computer graphics model of the gum surface, dentures or teeth and dental implants which allows the dental surgeon or technician to select the best shape for the overlying bridge of the superstructure.

In the case of a fixed dental prosthesis which is implant mounted (i.e. porcelain on metal), the ideal form of the superstructure can be automatically designed using the computer model taking into consideration the form of the laser camera imaged teeth and by subtracting a thickness of porcelain which the technician requires to recreate the shape of the imaged teeth. In the case of a dental prosthesis supported by a superstructure (overdenture), the shape of the superstructure can be automatically determined by taking into account the external shape of the prosthesis and by circulating the superstructure inside the prosthesis, making sure that the necessary thickness of prosthesis material (e.g. acrylic) will be available all around in order to provide a adequately strong prosthesis.

When precision forming the superstructure, it is possible to use various techniques. In one embodiment, the entire superstructure is cut using a CNC milling machine programmed to cut according to the shape data specified using the computer model. In another embodiment, the shape data is used to specify a 3D wax model prepared using stereolithographic techniques so that the superstructure can then be cast and then the abutments precision milled with a CNC milling machine. The casting metal may be titanium. In yet another embodiment, a CNC drilling machine could be equipped with a precision drill bit and used to provide a model with precision positioned implant abutment cavities. The shape of the superstructure can then be "crafted" by manually preparing the cavities for the rest of the superstructure in the model. Such crafting can be guided by the computer model. The superstructure can then be cast in the model and finished, with the abutments in precise position.

In accordance with a further general aspect of the present invention, there is provided a dental implant drill guide comprising a body having a first surface complimentary to a gum surface of a patient's jaw for allowing said body to be placed in mating relationship thereon with said body assuming a unique predetermined position relative to the patient's jaw, and at least one fixed orientation drill guide socket provided in said body for guiding a drill bit along a predetermined drill axis to a specific location on the gum surface when said body is in said predetermined position thereof.

In accordance with still further general aspect of the present invention, there is provided a dental implant superstructure for supporting a dental prosthesis over a gum surface of a patient's jaw, comprising a plurality of dental implant abutting flanges adapted to be securely seated against corresponding dental implants inserted in a patient's jawbone, a gum tissue overlying bridge, which is shaped in accordance with a computer model of the gum surface, the dentures of the dental prosthesis and the dental implants, for interconnecting said dental abutting flanges together in a fixed predetermined configuration in which said dental implant abutting flanges match said corresponding dental implants, said gum tissue overlying bridge offering a support structure having a shape established on the basis of said computer model so that the dental prosthesis be supported in a predetermined position on said gum tissue overlying bridge over the gum surface when said dental abutting flanges are securely seated on the dental implants.

In accordance with a still further general aspect of the present invention, there is provided a method of installing dental implants comprising the steps of: a) providing a dental implant drill guide having a first surface complementary to a gum surface covering a patient's jawbone and having drill guide sockets provided therein for guiding a drill bit along predetermined drilling axes while said guide is maintained in mating engagement with the gum surface; b) fitting said dental implant drill guide on said gum surface in a unique predetermined position; c) guiding the drill bit through said drill guide sockets and into the patient's jawbone to form holes therein for receiving corresponding dental implants; and, while said dental implant drill guide is still maintained in said unique predetermined position thereof, d) inserting the dental implants through said drill guide sockets and into the holes defined in the patient's jaw bone.

BRIEF DESCRIPTION OF THE DRAWINGS

Other objects and features of the present invention will be better understood by way of the following detailed description of the preferred embodiment with reference to the appended drawings in which:

FIG. 1 is a perspective view of an articulator supporting a physical model of a patient's upper and lower gums with dentures in place;

FIG. 2 is a perspective view similar to FIG. 1 in which the dentures have been replaced by a radiographic scanning guide;

FIG. 17 illustrates a similar computer graphics image as in FIG. 16 for a position between two implants;

FIG. 18 illustrates a perspective view of lower dentures and a lower superstructure; and FIG. 19 is a view from underneath the assembled components illustrated in FIG. 18.

DETAILED DESCRIPTION OF THE PREFERRED EMBODIMENT

Figure 3:
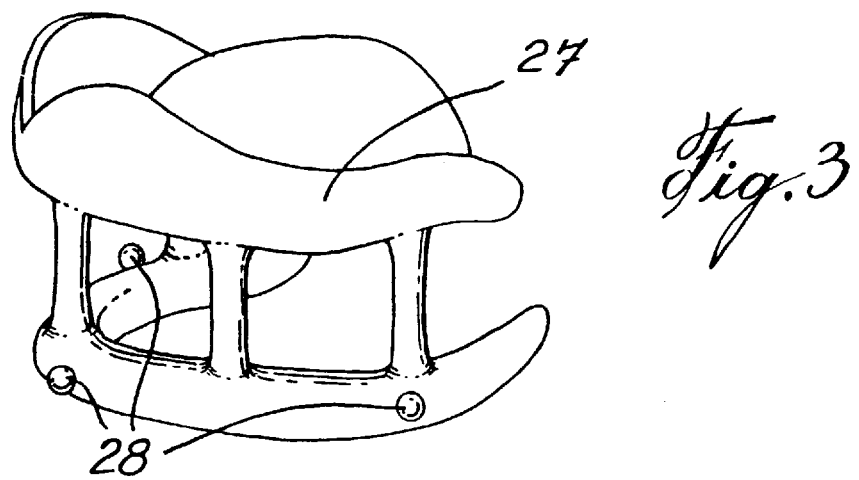
FIG. 3 is a perspective view of the radiographic scanning guide.

As illustrated in FIG. 1, an articulator 20 as is known in the art is set up to support a lower physical model 21 and an upper physical model 22 of a patient's mouth with lower and upper dentures 23 and 24 supported by the physical model with the teeth of the dentures in proper alignment. The articulator is adjusted using the adjustment means 25 and 26 as is known in the art. As illustrated in FIG. 2, the dentures 23 and 24 are removed and a scanner guide 27 is made by hand to fit exactly the space occupied by the upper and lower denture. Radio-opaque reference spheres 28 having a known diameter are bonded to the guide 27 with one sphere on each side at the rear and one in the front. In the illustration in the preferred embodiment, the spheres are shown near the lower jaw surface since it is the lower jaw that is to be imaged. The spheres could likewise be placed near the upper jaw surface as the case may be. The separated scanner guide body 27 is illustrated in FIG. 3.

The particular advantage of the scanner guide 27 according to the present invention is that during radiographic scanning of the patient's jaw, the patient may comfortably hold the scanner guide 27 in place by closing down on the same. As can be appreciated, the lower jaw could move during imaging and must be secured by means such as the scanner guide 27. The patient's head is held in place during radiographic scanning using a suitable brace as is known in the art.

Figure 4:
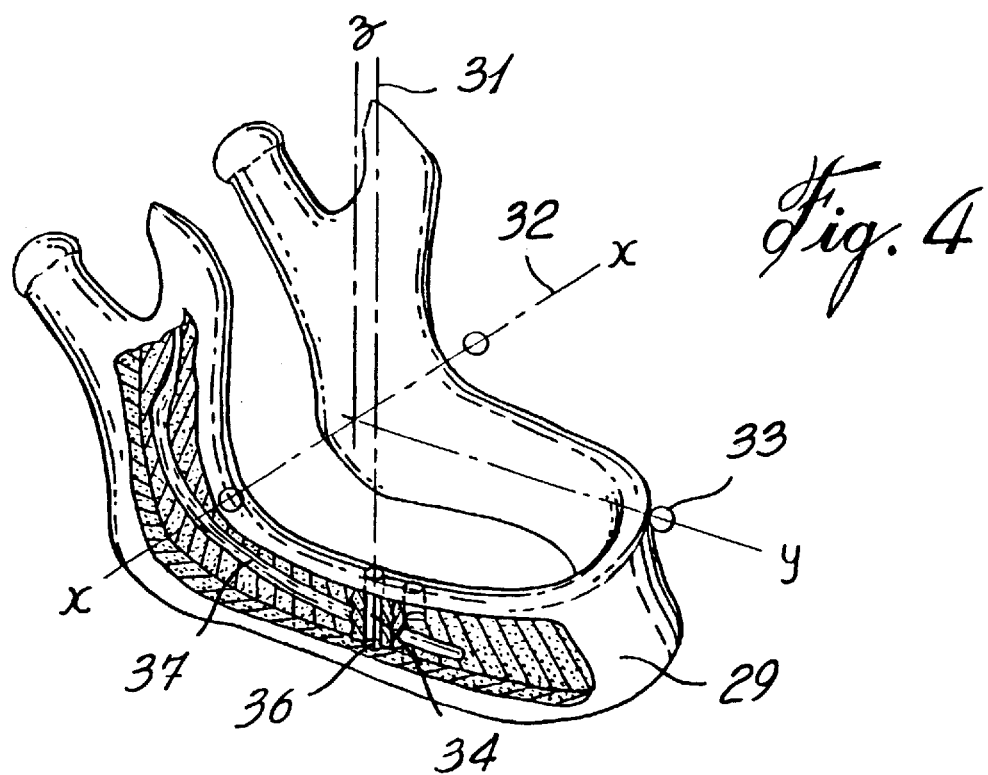
FIG. 4 is a perspective view of a three-dimensional computer model of a patient's lower jawbone shown partly broken away with the radio-opaque reference spheres and reference coordinate superimposed.

As shown in FIG. 4, the result of the radiographic scanning is to obtain a three-dimensional computer graphics model 29 of the patient's lower jaw. Images of the reference spheres 28 appear as 33 and provide a reference to a coordinate axes 32. The dental surgeon is capable of viewing with the model 29 the nerve 37 which extends from the base of the jaw until it exits the jawbone at each side of the chin. A drill axis 31 for each proposed drill hole 34 is selected on the computer model. The end point of the drill hole 36 is also selected.

For ease of selection of the drill axis 31, namely the position in space of the end point and the angular orientation of the drill axis 31, it may be possible to present slices of the computer model 29 to the dental surgeon or technician which would make it easier to select the parameters. As can be appreciated, two angles are required to specify the orientation of the drill axis 31, for example, a first angle θ may define an angle of the drill axis 31 with respect to the x-z plane and a second angular parameter φ may define the angle between the drill axis 31 in the z-y plane.

Figure 5:
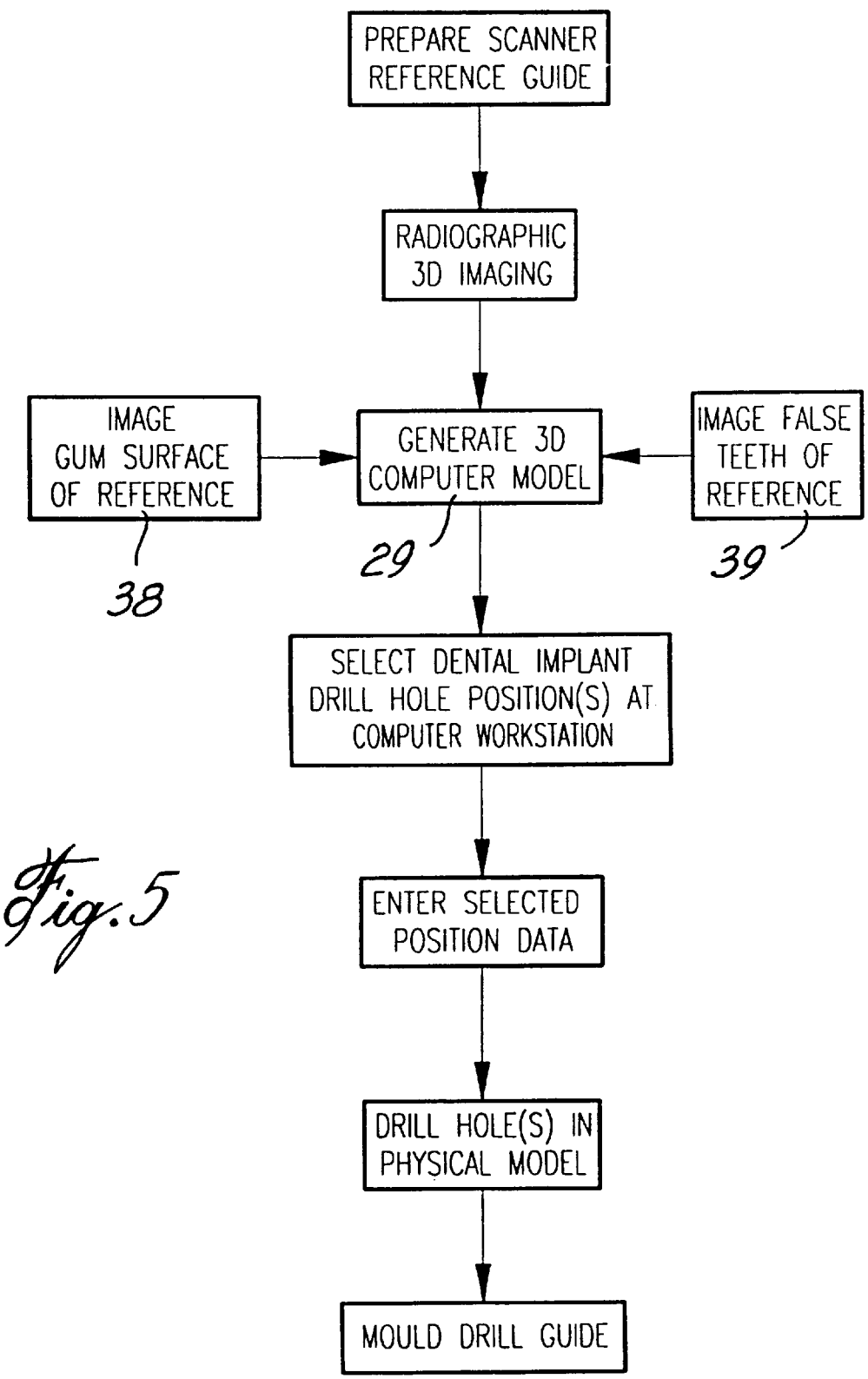
FIG. 5 is a flow diagram of the method of manufacturing the dental implant drill guide according to the preferred embodiment.
Figure 6:
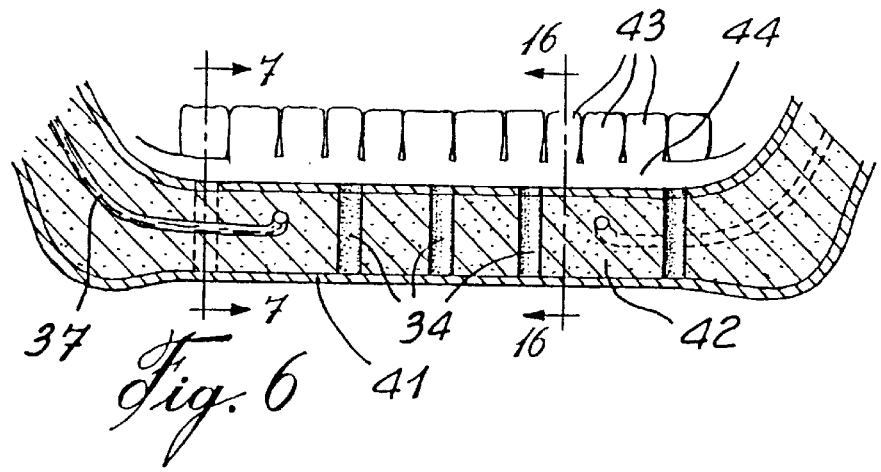
FIG. 6 is a panoramic view of a lower jawbone of a patient with the gum line and dentures superimposed.

In the preferred embodiment, selection of the drill axes 31 for the drill holes 34 is done with knowledge of the relative position of the gum surface and the relative position of the dentures or teeth. As illustrated in FIG. 5, the 3-D computer model 29 is built up using the radiographic 3-D imaging data as well as referenced gum surface image data and referenced denture image data. In FIG. 6, there is shown a panoramic slice view of the 3-D model 29 showing the gum surface 44 and dentures 43 superposed the cortical bone structure 41 and the marrow 42.

Figure 7:
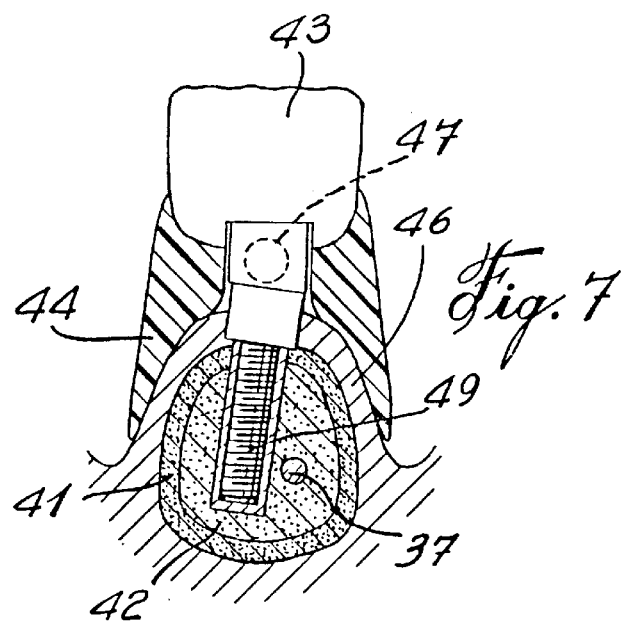
FIG. 7 is a cross-sectional view about line 7 of FIG. 6.
Figure 8:
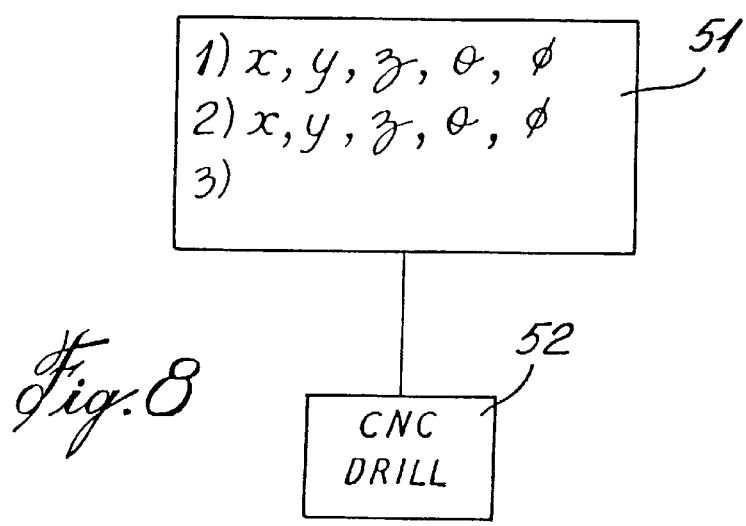
FIG. 8 is a block diagram of the CNC drill device and data entry terminal.

As illustrated in FIG. 7, in the preferred embodiment, it is possible to view for a selected drill axis 31 the resulting implant position 49 and how this relates to the bone structure 41 and 42, the nerve 37, if present, as well as the lower and upper denture structure 44 and 43. As can be appreciated, if the desired angle and position of the dentures with respect to the gum surface 46 would require an adjustment of the position and angle of the implant 49, the dental surgeon is able to select the optimum depth, position and angular orientation for the implant 49 relying entirely on the computer model. Once the hole termination position and angular orientation data for each of the drill holes is selected using the computer model, the data is entered through a data entry device 51 to control a CNC drill 52 in accordance with FIG. 8 and as better illustrated in FIG. 9.

The CNC drill 52 has a drill bit 53 which is capable of moving and drilling along a first vertical direction 54. The physical model 21 is mounted in such a way that it is able to turn about two directions 55 and 56 on a platform which is able to move in directions 57 and 60. The CNC drill 52 is capable of moving about five axes. In order for the CNC drill device to be properly referenced with respect to the physical model 21, the scanner guide may be placed on top of the physical model 21 and a coordinates measuring machine (CMM) connected to CNC drill 52 is used to accurately locate the position of each one of the position reference spheres and reference these to the CNC drill's reference frame. The CNC drill 52 is then programmed to convert the hole position and orientation data as referenced to the frame of reference of the computer model to the reference frame of the CNC drill so that the drill holes may be prepared in the physical model 21.

Figure 10:
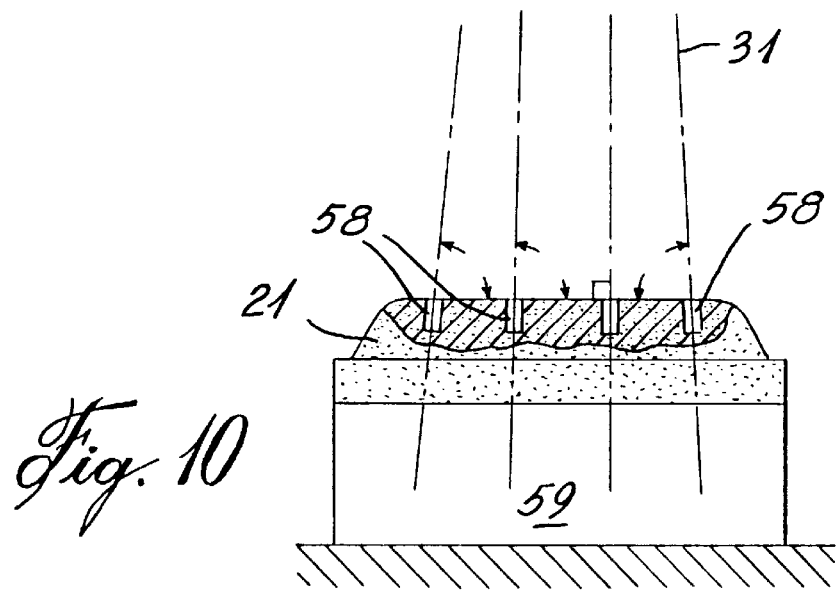
FIG. 10 is a front view of a physical model with four drill axes shown.

As illustrated in FIG. 10, four drill holes 58 are cut into the physical model 21 which is mounted on a base 59. The drill hole axes 31 as shown are in different positions and orientations.

Figure 11:
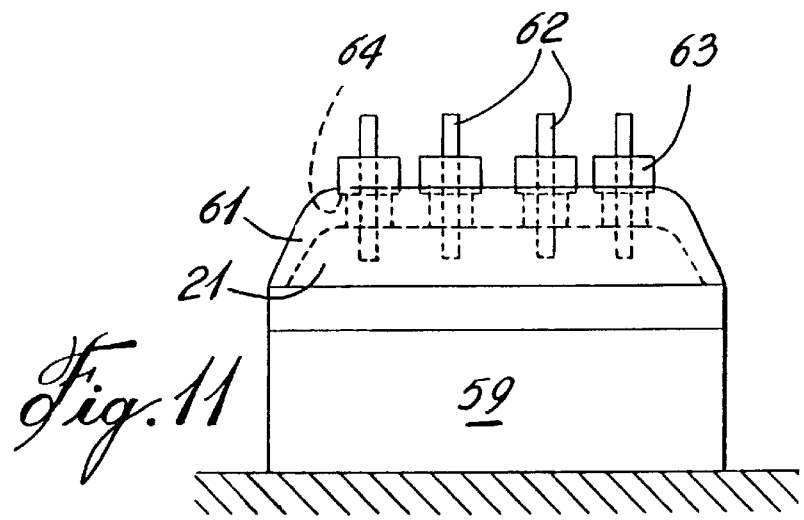
FIG. 11 is a view similar to FIG. 10 in which a drill guide has been molded with the fixed drill sockets formed by pins inserted in the drill holes.

As shown in FIG. 11, rods 62 are inserted into the holes 58. The socket forming mold parts 63 are placed over the rods 62 and a surrounding mold structure (not shown) is placed around the physical model 21 to allow for the molded guide body 61 to be formed. Since the holes 58 are of different heights, the socket forming mold parts 63 are adjusted in size such that the distance between the circular flange edge and the end of the rods 102 is a constant. In this way, the circular flange edge 64 of the drill guide sockets is at a fixed distance with respect to the desired end point of the drill hole.

Figure 12:
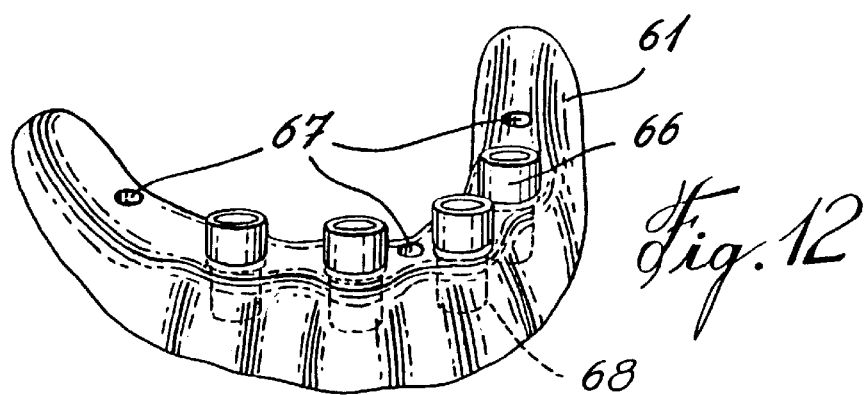
FIG. 12 is a perspective view of the drill guide according to the preferred embodiment.
Figure 13:
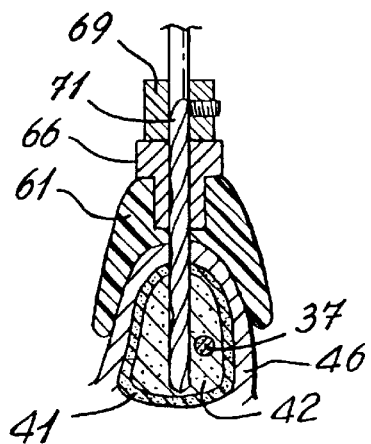
FIG. 13 is a sectional view of the drill guide being used to drill a patient's jawbone.

As shown in FIG. 12, the finished molded drill guide body 61 has a plurality of drill guide tubes 66 inserted into the drill guide sockets 68, and three holes 67 are additionally provided for transitionally securing the drill guide 61 to the patient's jawbone during surgery. The drill guide tubes 66 may be removed and reinserted into the drill guide sockets 68 in order to change the internal diameter of the drill guide tubes as is required during surgery since the implant drill hole is started with a very small diameter drill bit and subsequently larger drill bits are used until the full size implant drill hole is obtained. As shown in FIG. 13, the drill used in surgery is provided with a collar 69 for abutting against the upper surface of the guide tube 66 in such a way that the distance between the bottom of the collar 69 and the end of the drill bit 71 is fixed as required. In the preferred embodiment, the collar 69 is integral with the drill bit 71.

As can be appreciated, the oral surgeon prepares the implant holes using the drill guide 61 by removing circular portions of the gum (gingival taps) at the implant sites. In the conventional method of drilling implant holes, a procedure known as "flap surgery" is carried out in which a piece of the gum covering the jawbone where the implant hole is to be drilled is cut and peeled back so that the oral surgeon has clear access to the jawbone surface. Using the present invention, the surgeon has the option of doing flap surgery if required or circumferential surgery as needed. Of course, if a conventional flap surgery is to be done, a modification of the surgical guide should be done, i.e. the guide should be removable as needed for flap surgery. In order to put the guide back at the same location, the use of transitional implants is needed to seat the guide after the flap is done. If the circular approach is chosen, there is no need to remove the guide during surgery, and by avoiding flap surgery, post operation healing time should be reduced.

Figure 14:
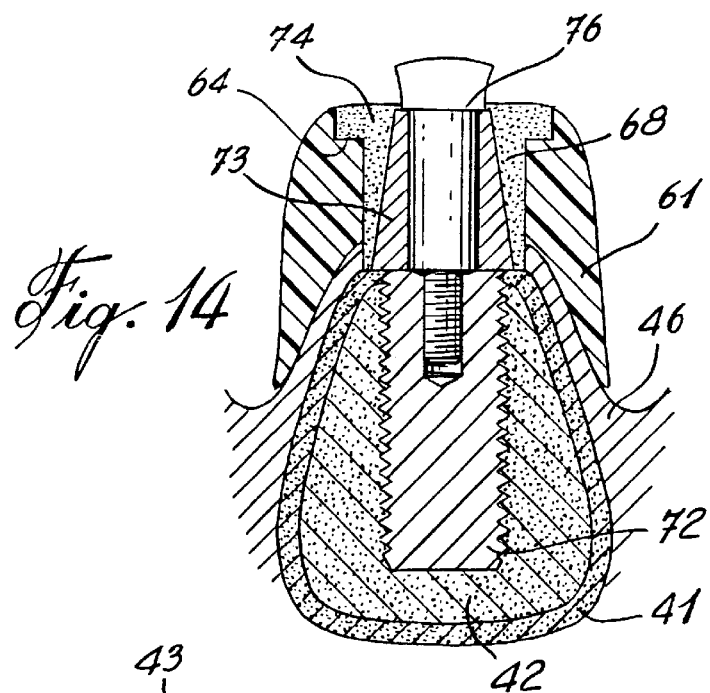
FIG. 14 is an enlarged sectional view of a jawbone having received an implant with the drill guide placed on top of the gum surface to act as an impression tray for the purposes of taking an exact imprint of the implant position using a transfer.

As illustrated in FIG. 14, the oral surgeon screws in an implant 72 into the hole made using drill guide 61. This can be done with the drill guide 61 remaining in place, the implants being inserted through the sockets 68. The upper surface of the implant 72 is approximately flush with the upper surface of the cortical exterior 41 of the jawbone. The implant 72 has a hollow threaded core. Since the implant 72 has been inserted into the jawbone tissue 42 by hand, its exact position may not be perfectly defined by the drill hole formed using the drill guide.

Figure 15:
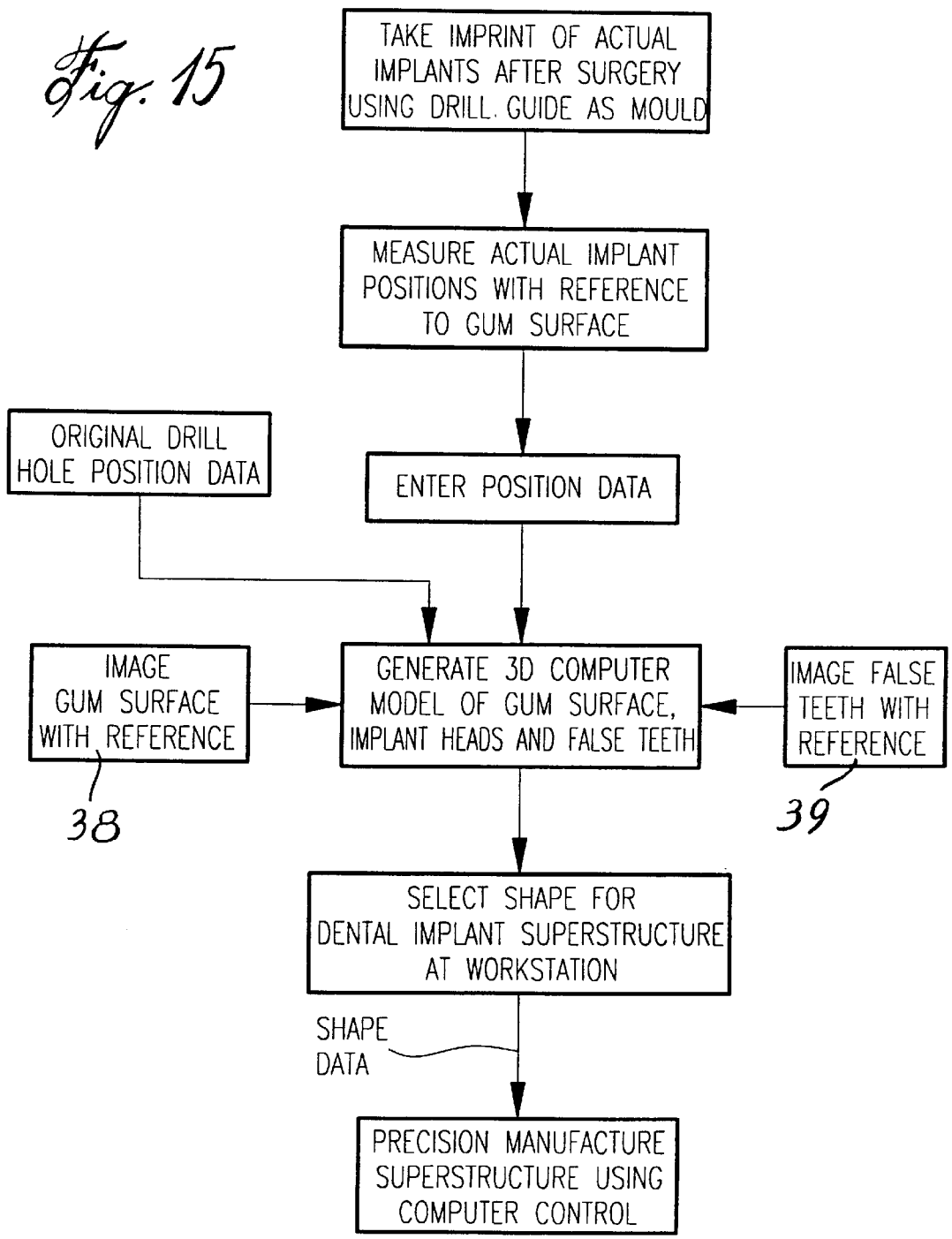
FIG. 15 is a flow diagram of the method for machining a superstructure according to the preferred embodiment.

Once the implants have been secured in place, a transfer 73 is placed over the implant 72 and a central screw 76 is used to fasten the transfer 73 to the implant 72. An imprint material 74 is injected in the space between the drill guide cavity 68 and the transfer 73. The imprint material hardens after a short period of time and the oral surgeon or dentist removes the screws 76 which allows the drill guide 61 to be removed with the transfers 73 secured in place with a precise correspondence to the actual positions of the implants 72 in the patient's jawbone. As illustrated in FIG. 15, the transfers securely lodged within the drill guide are used as a physical recording of the implant positions. The implants are then capped with screws and the patient is typically given a period of a few months to recover from the insertion of the implants. During this time, the superstructure to be attached to the implants can be prepared.

As shown in FIG. 15, the method for machining the superstructure according to the preferred embodiment requires measuring the actual implant position with reference to the gum surface. This is done by securing implant analogs (replicas of the implants) to each transfer. Then, with a special moldable stone material used in the art for producing oral cavity replicas, the analogs are embedded in the moldable stone material until it sets. After unscrewing all of the transfers from the analogs, a duplicate of the patient's mouth and positions of the implants is obtained. Extensions of the implants which are precisely machined to fit the analogs are screwed back into each analog and CMM measurements are made of the extensions. The extensions referred to as "targets" are used because the implant analog is typically too small for the CMM sensor and the target gives the technician additional surface to measure the top of the target and the sides. The position of each implant is then calculated knowing the position of each target, the targets being of precise known size and shape. It is noted that by changing the occluded (top) surface of the analogs, it is possible to measure the position of the implants by using the CMM directly on the analogs without using the said targets. It is also noted that the same measurement could be calculated by directly scanning the position of the analogs with the said laser scanning camera.

To be able to accurately superimpose the image of the gum surface and the image of the proposed teeth requires obtaining in addition to the positions of the actual implants, a fixed reference to the patient's gum surface/jawbone. As can be appreciated, this can be achieved in many different ways. Known reference points may be provided on the drill guide and these can be measured when the drill guide is attached to the analogs on the stone physical model using the CMM apparatus. If the scanner guide is able to be fit securely over the gum surface of the physical model in which the implant analogs are embedded, the three spheres of the scanner guide can be measured before the targets are screwed in place.

Alternatively, the implant positions could be measured by attaching measurement targets directly to each transfer while measuring additionally reference points on the drill guide. This, however, poses the problem of solidly securing and mounting the drill guide to the CMM table.

The result of the CMM measurement starting with the transfers embedded in the drill guide is to obtain actual implant position data with a reference to the gum surface.

A 3-D computer model of the gum surface implant heads and teeth (overdentures) is then generated using the referenced gum surface image 38 and the referenced teeth image 39. Also, the original drill hole position data is entered into the 3-D computer model in order to monitor the shifts between the desired and the actual implant positions. This also permits the oral surgeon to confirm whether the actual implant positions are different in a way which could potentially create problems. It also serves to confirm that the measured actual implant positions are accurate.

Figure 16:
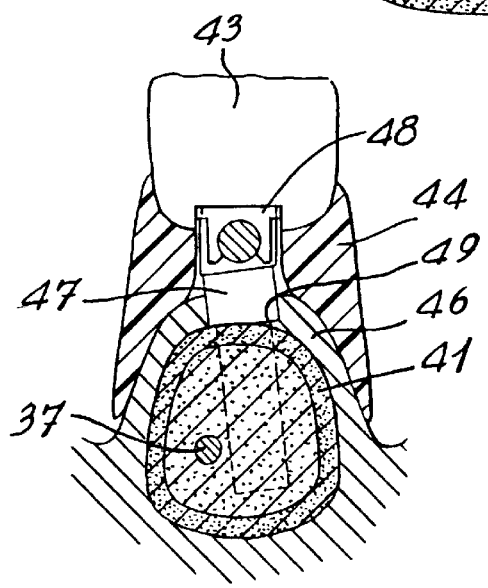
FIG. 16 is a sectional view of a computer model illustrating the denture fit over the patient's gums with the implant head in correct relative position.

As illustrated schematically in FIGS. 16 and 17, the 3-D computer model can be used to show sectional views transverse to the denture and upper jaw structure to illustrate the actual position of the implant, gum surface and teeth structure. As shown in FIG. 16, the implant head 49 will receive a superstructure consisting of an abutment foot 47 extending down to the top of the implant and having an upper bridge-like structure 48 extending inside the lower portion 44 of the denture structure and even possibly into the upper portion 43 of the denture structure. In between two implants, as illustrated in FIG. 17, the bridge structure 48 is designed to be located above the gum surface 46 and within the denture structure. As can be appreciated, due to the confines and configuration of the patient's mouth, it may be necessary to shape the bridge structure 48 such that it passes close to either an inner or outer side wall of the denture structure 43, 44. In this way, the denture technician is capable of viewing in the computer model how the bridge structure and superstructure is best constructed.

Figure 9:
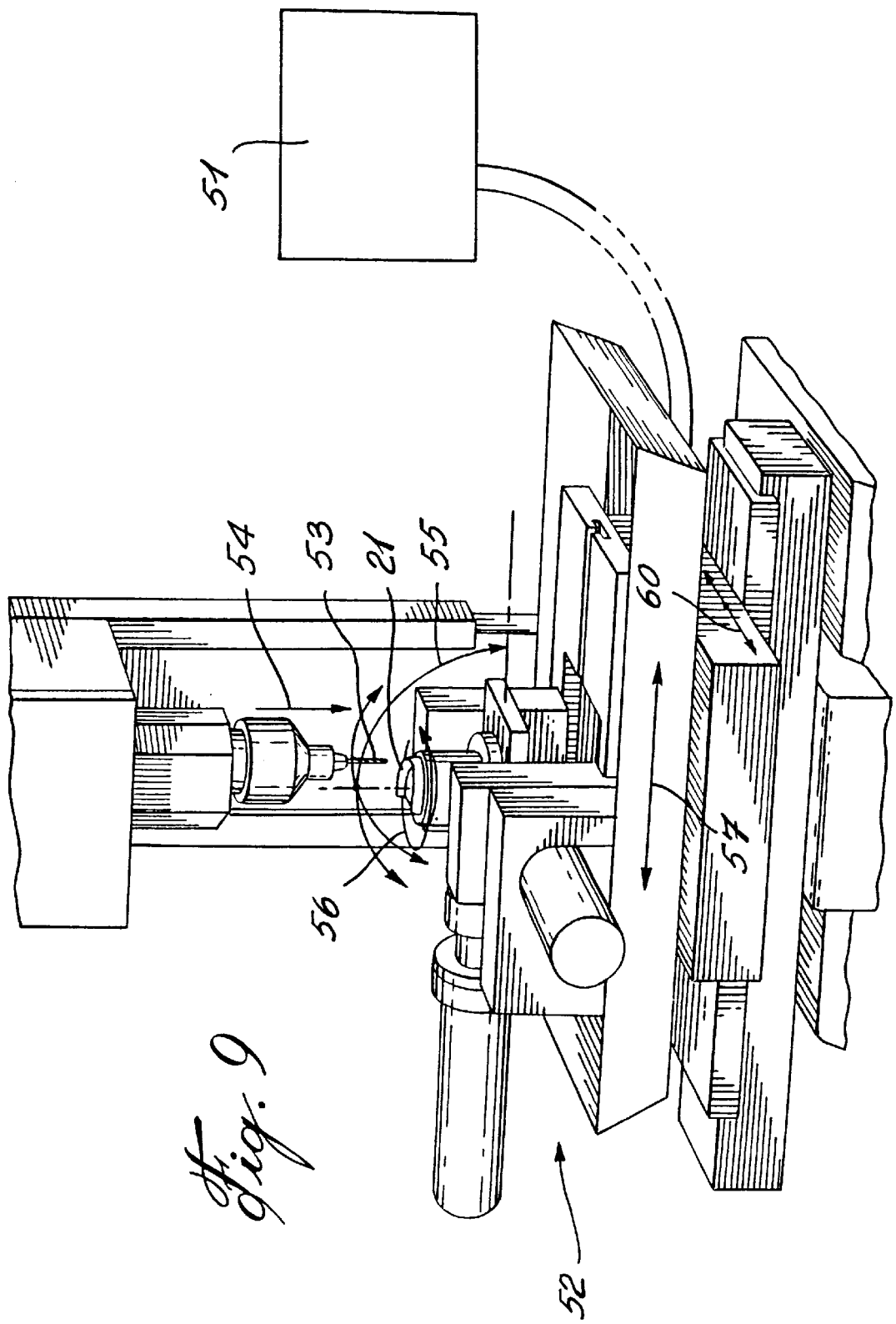
FIG. 9 is a perspective view of a five axis CNC drill device.

As shown in FIG. 15, once the denture technician has selected the shape for the dental implant superstructure using the computer model, the shape data is passed on to a precision forming device for shaping the superstructure. In the preferred embodiment, a CNC milling machine similar to the CNC drill device illustrated in FIG. 9 is used. The result is a superstructure as illustrated in FIG. 17 which may be fastened directly to the dental implants. The superstructure illustrated in FIG. 17 is of the type which receives dentures by snap-fit as is illustrated in FIG. 18. The superstructure will be prepared from a solid piece of commercially pure titanium or any biocompatible material such as porcelain, preventing corrosion between implants and superstructure.

Alternatively, and especially when the shape of the superstructure is more complex, stereolithography is used to create a 3D superstructure in wax. The wax superstructure can be used according to known techniques to obtain a cast titanium or titanium alloy superstructure body of the same shape. Precision holes and seats for the implants are then machined in the superstructure body using a 5-axis milling machine.

What is claimed is:

1. A dental implant superstructure for supporting a dental prosthesis over a gum surface of a patient's jaw in which a number of dental implants have been inserted comprising:
   a body of one-piece construction shaped on the basis of a computer model of the patient's gum surface, the dentures of the dental prosthesis and the dental implants, said body being made of a homogeneous bio-compatible material and defining:
   a plurality of dental implant abutting flanges adapted to be securely seated against corresponding dental implants inserted in a patient's jawbone, and
   a gum tissue overlying bridge interconnecting said dental abutting flanges together in a fixed predetermined configuration in which said dental implant abutting flanges match said corresponding dental implants, said gum tissue overlying bridge offering a support structure having a shape established on the basis of said computer model so that the dental prosthesis be supported in a predetermined position on said gum tissue overlying bridge over the gum surface when said dental abutting flanges are securely seated on the dental implants.

2. A dental implant superstructure as defined in claim 1, wherein said gum tissue overlying bridge is curved so as to span over the whole patient's jawbone.

3. A dental implant superstructure as defined in claim 1, wherein each said dental implant abutting flanges are provided at a distal end of a cylinder depending from said gum tissue overlying bridge.

4. A dental implant superstructure as defined in claim 3, wherein each said cylinder defined an axially extending through bore adapted to receive a fastener for securing said cylinder to an underlying dental implant.

* * * * *